United States Patent [19]
Grandine et al.

[11] 3,947,345
[45] Mar. 30, 1976

[54] APPARATUS FOR ELECTROPHORESIS MIGRATION

[75] Inventors: Joseph D. Grandine, Acton, Mass.; Nat H. Marsh, Nashua, N.H.; James E. Snyder, Brighton, Mass.

[73] Assignee: Millipore Corporation, Bedford, Mass.

[22] Filed: Nov. 15, 1974

[21] Appl. No.: 524,069

[52] U.S. Cl. ......... 204/299 R; 23/230 B; 204/180 S; 204/180 G
[51] Int. Cl.² .................. G01N 27/26; G01N 27/28
[58] Field of Search ............ 204/180 G, 180 S, 299; 23/230 B

[56] References Cited
UNITED STATES PATENTS

| | | | |
|---|---|---|---|
| 3,407,133 | 10/1968 | Oliva et al. | 204/299 |
| 3,616,456 | 10/1971 | Valmet | 204/299 |
| 3,798,152 | 3/1974 | Cawley | 204/299 |
| 3,839,184 | 10/1974 | Richter | 204/299 |
| 3,856,656 | 12/1974 | Brink | 204/299 |

*Primary Examiner*—G. L. Kaplan
*Assistant Examiner*—A. C. Prescott
*Attorney, Agent, or Firm*—Kenway & Jenney

[57] ABSTRACT

Apparatus for producing electrophoretic migration in an agarose gel slide which includes a slide mounting block containing a salt which maintains slide temperature during electrophoresis processing.

14 Claims, 2 Drawing Figures

3,947,345

APPARATUS FOR ELECTROPHORESIS MIGRATION

FIELD OF THE INVENTION

This invention relates in general to electrophoresis and more particularly to apparatus for producing electrophoretic migration in an agarose gel slide while maintaining a substantially constant and relatively low temperature in the slide.

BACKGROUND OF THE INVENTION

Electrophoresis is a method for the analysis of proteins in body fluids and has proven to be very valuable in laboratory and clinical work. There have been a number of commercial instruments produced for relatively low resolution applications, in which the electrophoretic medium is a microporous plastic membrane or a polyacrylamide gel which permits resolution of perhaps five components in the material being analyzed. Much higher resolution and accordingly analysis of as many as 15 components may be obtained utilizing a relatively large area of agarose gel slide which is subjected to electrophoresis under specific controlled conditions. Such a slide is formed of an agarose gel with a barbital buffer added. While measurements performed with these slides have shown excellent results in laboratory environments, in order to attain wide spread clinical use, an apparatus for providing easy, economical and particularly accurate and reproducible results is required.

In electrophoresis, the initial step is to apply the sample material to the electrophoretic medium and allow the separation to take place by migration under the influence of an applied electric field. Thereafter the slide is fixed chemically, dried and subsequently read either directly or with appropriate densitometer devices. To obtain a practical migration apparatus, the device must be capable of obtaining accurate and highly reproducible results even when operated by relatively unskilled technicians. In order to provide such accuracy and reproducibility, there are a number of variables which must be precisely controlled. These include the value of the applied voltage, the time duration for migration, the voltages applied, the geometry of mounting and holding the slide during the period of migration and the temperature maintained during the period of migration.

For a large area of slide, for example, a rectangular slide approximately 9 inches by 6 inches, with an applied voltage of approximately 200 volts, the slide would undergo an increase in temperature to values above 55°C. At these elevated temperatures, drying of the slide occurs with an increase in ionic concentration, in turn causing further power dissipation and further increase in temperature. Additionally, denaturing of proteins takes place at these high temperatures. Finally, it is desirable to maintain the slide in a constant temperature environment during electrophoresis. Variations in slide temperature during separation, while not affecting information content, do cause variations in mobility of individual protein components during electrophoresis. By performing electrophoretic separation at a constant temperature comparison of patterns between slides is facilitated. In the past, various conventional cooling techniques have been employed. These include both water cooling a member in thermal contact with the slide and various air cooling approaches. For a slide which must necessarily have each of its ends inserted in a chemically active buffer material and have a voltage of approximately 200 volts applied across it, such cooling arrangements complicate the design of the migration apparatus and render it somewhat difficult to manipulate in routine laboratory procedures.

It is, therefore, the primary object of the present invention to provide an electrophoresis migration apparatus allowing for use of handling, economy of operation, and precise results, while maintaining the electrophoretic slide at a substantially constant temperature between 5°C and 40°C.

SUMMARY OF THE INVENTION

Broadly speaking, in the present invention, a rectangular electrophoresis slide is mounted with the substrate protion of the slide in intimate contact with an external concave cylindrical surface of the mounting block. The interior of the block contains salts, which melt at a temperature a few degrees above room temperature as for example about 29°C. The heat required to liquefy the salt is removed from the surface which is in contact with the slide. This concave surface is formed of a material which is electrically insulating, hydrophobic, and does not interact chemically with the buffer material. The mounting block is configured to be positioned in a sealed relationship with a buffer reservoir divided into two isolated buffer cells, each containing the appropriate barbituate buffer solution, and each having an opposite polarity electrode in contact with the solution. A power supply for providing appropriate voltage at sufficient power levels is connected between the two electrodes. The slide mounting block is arranged to provide for positive retention of the slide compressed sufficiently to ensure continuous intimate contact between the substrate of the slide and the concave surface of the mounting block. With the slide so positioned, when the mounting block is placed over the reservoir, the ends of the slide are located within the buffer solution and, when the voltage is applied, the electrophoretic migration takes place.

THE DRAWINGS

In the drawing:

FIG. 1 is an illustration generally in perspective view of a mounting block and buffer reservoir assembly constructed in accordance with the principles of this invention; and FIG. 2 is an illustration in cross sectional view taken along the lines 2—2 of FIG. 1.

DESCRIPTION OF PREFERRED EMBODIMENTS

Figure 1:
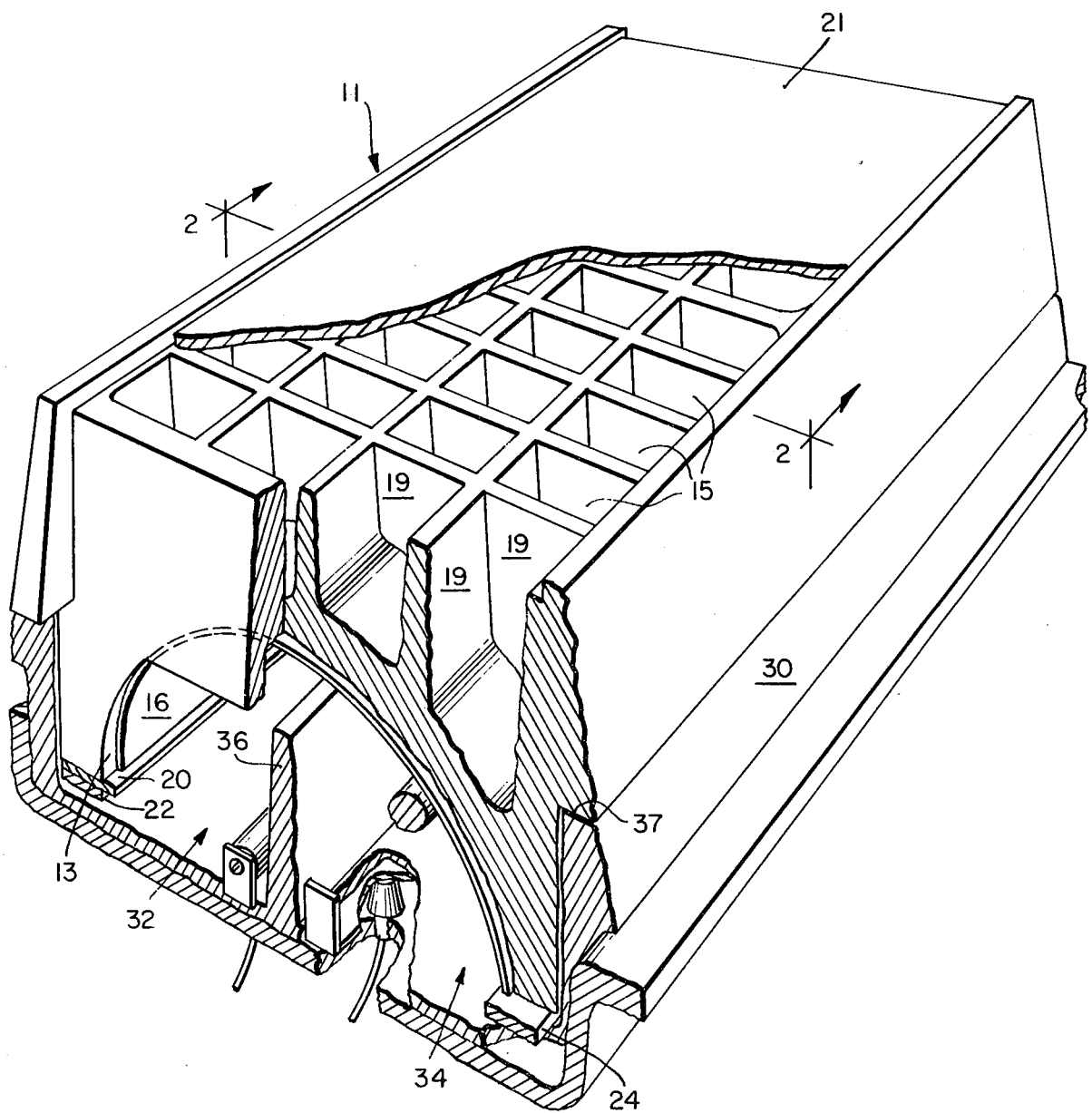
Figure 2:
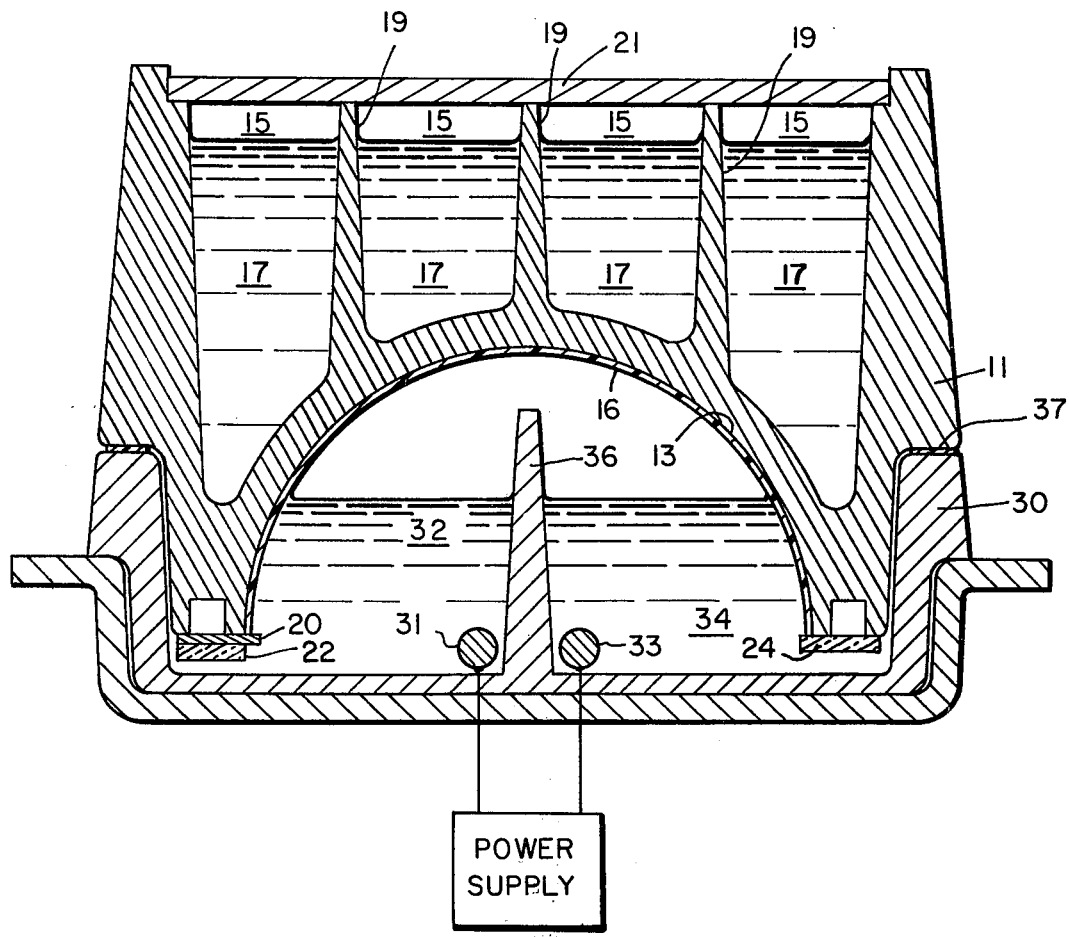

With reference now to FIG. 1, the mounting and cooling block generally indicated at 11 is formed of an aluminum casting and includes a concave cylindrical external surface 13. In the hollow portions 15 of the mounting block 11 a material 17, such as lithium salt, is located. The mounting block may be formed with internal cooling fins 19, and includes a cover 21 which may be sealably attached to the mounting block 11 itself, by means of screws or the like (not shown). The concave surface 13 is preferably coated with an electrically insulating material, which is chemically nonreactive with the buffer solution and which should also be hydrophobic in order to avoid wetting of the cooling block which would result in an uneven temperature distribution across the surface of the electrophoretic slide. A suitable material is a coating of polyphenylene sulfide resin, such as that manufactured under the trademark Ryton by Phillips Petroleum Company of Bartelsville, Oklahoma, U.S.A. An electrophoretic slide 16 is shown mounted in continuous intimate contact with the concave surface 13. The slide is formed of an agarose gel layered on a substrate of polyethylene terephthalate. Typical dimensions for the slide are 6 inches wide by 9.24 inches in length, with the polyethylene terephthalate substrate having a thickness of 0.007 inches. In order to provide for ease in handling the agarose gel covers the entire surface of the slide, with the exception of a ¾ inch strip along each of the long sides of the polyethylene terephthalate substrate. In handling, the slides can then be handled along these ¾ inch strips, without contamination of the agarose gel material.

The material 17 is any suitable material which has a phase change in the desired range and the property of absorption of sufficient heat associated with the phase change to maintain the slide at a constant temperature. We have found that certain salts are particularly useful for this purpose, the phase change being from a solid to a liquid phase. One salt which we have used is hydrated lithium nitrate. The cooling block 11 includes about 800 milliliters of this material, which has a heat fusion of about 70 calories per gram. This material is also desirable because of its relatively high density, so that a significant amount of the material will occupy a relatively small volume.

To position the slide on the mounting block 11, the slide is moved, with the substrate side uppermost, into position so that one end presses against a compressible lip element 20, which typically could be formed of silicon, or rubber or other soft resilient material, which is inert to the buffer solution. The lip 20 is held in position by a retainer 22, formed of glass filled board or other equivalent material. The opposite end of the slide 16 is then allowed to slip under the retaining element 24 and the resilient lip 20 retains the slide generally in compression against the concave surface 13 to provide for continuous intimate contact. The retaining element 24 may also be formed of glass filled board. Alternative arrangements for retaining the slide include the use of spring retaining elements.

The buffer reservoir 30 which may be formed, for example, of cast epoxy, includes two isolated buffer cells 32 and 34 with a relatively high separator 36 between them. One electrode 31 lies within the buffer cell 32, while an identical electrode 33 lies within the buffer solution cell 34. The upper edge of the reservoir member 30 contains a sealing gasket 37 to avoid spillage of the buffer solution when the mounting block 11 is placed in position on the reservoir 30. In operation a power supply, capable of providing a voltage of approximately 200 volts at a peak amperage of approximately 300 amps. is connected between electrodes 31 and 33. A typical migration time is in the order of 45 minutes to 1 hour.

The buffer solution may be any suitable electrophoresis buffer solution such as a mixture of 0.331 gms of diethyl barbituric acid +1.848 gms of sodium diethyl barbiturate to 120 mils. of distilled water (pH 8.6, ionic strength 0.075).

It has been found that with the material 17 described above, the mounting block may be utilized to process as many as four slides, before it needs to be recycled. The recycling of the mounting block consists in allowing it to stand overnight at room temperature so that the salt may solidify or, if a shorter recycling time is desired, the block may be recycled by placing it for about one hour in an ice bath.

While a specific geometric configuration of the apparatus has been described, and specific materials have been given as examples, it will be understood that other materials may be employed with other configurations and that the invention should be construed as being defined by the associated claims.

We claim:

1. An apparatus for effecting electrophoretic migration on an electrophoresis slide comprising:
   a mounting block having an electrically insulating thermally conducting contact surface;
   means for mounting said electrophoresis slide in substantially continuous intimate contact with said contact surface;
   a material, solid at room temperature, which absorbs heat while undergoing a phase change enclosed within said mounting block in thermal contact with said block to absorb heat from said electrophoresis slide by absorbing heat during the process of electrophoresis to maintain said slide at a substantially constant temperature;
   reservoir means for containing two isolated portions of buffer solution; and
   first and second electrodes, said first electrode being in electrical contact with said first portion of buffer solution and said second electrode being in electrical contact with said second portion of buffer solution, said reservoir and said cooling block being configured such that said cooling block may be placed in position with respect to said reservoir such that an electrophoresis slide mounted on said block has one end protruding into said first portion of buffer solution and the opposite end protruding into the other portion of said buffer solution.

2. Apparatus in accordance with claim 1 wherein said heat absorbing material is lithium salt.

3. Apparatus in accordance with claim 1 in which said phase change is from a solid to a liquid.

4. An apparatus for effecting electrophoretic migration on an electrophoresis slide comprising:
   a mounting block having an electrically insulating thermally conducting contact surface and formed as a generally rectangular hollow block having one external surface formed as a concave cylinder to serve as said contact surface;
   means for mounting said electrophoresis slide in substantially continuous intimate contact with said contact surface;
   a material which absorbs heat while undergoing a phase change enclosed within said mounting block in thermal contact with said block to absorb heat from said electrophoresis slide by absorbing heat during the process of electrophoresis to maintain said slide at a substantially constant temperature;
   reservoir means for containing two isolated portions of buffer solution; and
   first and second electrodes, said first electrode being in electrical contact with said first portion of buffer solution and said second electrode being in electrical contact with said second portion of buffer solution, said reservoir and said cooling block being configured such that said cooling block may be placed in position with respect to said reservoir such that an electrophoresis slide mounted in said block has one end protruding into said first portion of buffer solution and the opposite end protruding into the other portion of said buffer solution.

5. Apparatus in accordance with claim 4 wherein said hollow block includes radiating fins in contact with said heat absorbing material contained therein.

6. Apparatus in accordance with claim 5 wherein said mounting block is formed of aluminum.

7. Apparatus in accordance with claim 5 wherein said concave surface is coated with a hydrophobic insulating material.

8. Apparatus in accordance with claim 7 wherein said material is polyphenylene sulfide resin.

9. In an apparatus for effecting the electrophoretic migration of an electrophoresis slide, the improvement comprising;
    a mounting block having an electrically insulating thermally conducting contact surface;
    means for mounting said electrophoresis slide in substantially continuous intimate contact with said contact surface; and
    a material, solid at room temperature, which absorbs heat while undergoing a phase change enclosed within said mounting block in thermal contact with said block to absorb heat from said electrophoresis slide by changing phase during the process of electrophoresis to maintain said slide at a substantially constant temperature.

10. In an apparatus for effecting the electrophoretic migration of an electrophoresis slide, the improvement comprising;
    a mounting block having an electrically insulating thermally conducting contact surface and formed as a generally rectangular hollow block having one external surface formed as a concave cylinder to serve as said contact surface;
    means for mounting said electrophoresis slide in substantially continuous intimate contact with said contact surface; and
    a material which absorbs heat while undergoing a phase change enclosed within said mounting block in thermal contact with said block to absorb heat from said electrophoresis slide by changing phase during the process of electrophoresis to maintain said slide at a substantially constant temperature.

11. Apparatus in accordance with claim 9 in which said phase change is from a solid to a liquid.

12. Apparatus in accordance with claim 9 wherein said material is a lithium salt.

13. Apparatus in accordance with claim 10 wherein said hollow block includes radiating fins in contact with said heat absorbing material.

14. Apparatus in accordance with claim 13 wherein said mounting block is formed of cast aluminum.

* * * * *

UNITED STATES PATENT AND TRADEMARK OFFICE
CERTIFICATE OF CORRECTION

PATENT NO. : 3,947,345
DATED : March 30, 1976
INVENTOR(S) : Joseph D. Grandine, Nat H. Marsh, James E. Snyder It is certified that error appears in the above–identified patent and that said Letters Patent are hereby corrected as shown below:

Column 2, line 10 "use" should read --ease--.

Signed and Sealed this

Thirteenth Day of July 1976

[SEAL]

Attest:

RUTH C. MASON
*Attesting Officer*

C. MARSHALL DANN
*Commissioner of Patents and Trademarks*